(12) United States Patent
von Hoffmann

(10) Patent No.: US 8,939,931 B2
(45) Date of Patent: *Jan. 27, 2015

(54) INTRAVASCULAR ACCESS CATHETER

(75) Inventor: Gerard von Hoffmann, Trabuco Canyon, CA (US)

(73) Assignee: Onset Medical Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/549,857

(22) Filed: Jul. 16, 2012

(65) Prior Publication Data

US 2012/0283633 A1    Nov. 8, 2012

Related U.S. Application Data

(60) Continuation of application No. 11/936,632, filed on Nov. 7, 2007, now Pat. No. 8,231,600, which is a division of application No. 10/623,875, filed on Jul. 21, 2003, now Pat. No. 7,309,334.

(60) Provisional application No. 60/398,071, filed on Jul. 23, 2002.

(51) Int. Cl.
| | | |
|---|---|---|
| *A61M 29/00* | (2006.01) | |
| *A61M 31/00* | (2006.01) | |
| *A61B 17/22* | (2006.01) | |
| *A61M 25/00* | (2006.01) | |
| *A61B 17/34* | (2006.01) | |
| *A61M 27/00* | (2006.01) | |

(52) U.S. Cl.
CPC ........ *A61M 25/0021* (2013.01); *A61B 17/3439* (2013.01); *A61B 17/22* (2013.01); *A61M 25/0023* (2013.01); *A61M 27/002* (2013.01); *A61B 2217/005* (2013.01); *A61M 25/0043* (2013.01)
USPC ...... 604/96.01; 604/523; 604/526; 604/95.04

(58) Field of Classification Search
USPC .............. 604/523–530, 156–158, 96.01, 118, 604/95.04, 104–107, 264, 537, 95.01
See application file for complete search history.

(56) References Cited

U.S. PATENT DOCUMENTS

| | | |
|---|---|---|
| 2,042,900 A | 6/1936 | James |
| 4,403,612 A | 9/1983 | Fogarty |
| 4,601,713 A * | 7/1986 | Fuqua ........................... 604/514 |
| 4,646,736 A | 3/1987 | Auth |
| 4,692,139 A | 9/1987 | Stiles |
| 4,706,671 A | 11/1987 | Weinrib |
| 4,710,181 A | 12/1987 | Fuqua |
| 4,716,901 A | 1/1988 | Jackson et al. |
| 4,738,666 A | 4/1988 | Fuqua |
| 4,739,768 A | 4/1988 | Engelson |

(Continued)

FOREIGN PATENT DOCUMENTS

| | | |
|---|---|---|
| EP | 0 177 177 | 9/1985 |
| EP | 0 249 456 | 6/1987 |

(Continued)

*Primary Examiner* — Quynh-Nhu H Vu
(74) *Attorney, Agent, or Firm* — Inskeep IP Group, Inc.

(57) ABSTRACT

Disclosed is an access catheter, having a distal segment which is moveable from a reduced outside diameter for positioning at a target site, and an enlarged outside diameter to create an enlarged internal working lumen. In one application, the catheter is configured for use as an intracranial aspiration catheter. Methods are also disclosed.

19 Claims, 9 Drawing Sheets

(56) References Cited

U.S. PATENT DOCUMENTS

| | | | |
|---|---|---|---|
| 4,798,193 A | 1/1989 | Giesy et al. | |
| 4,820,349 A | 4/1989 | Saab | |
| 4,846,791 A | 7/1989 | Hattler et al. | |
| 5,011,488 A | 4/1991 | Ginsburg | |
| 5,066,285 A | 11/1991 | Hillstead | |
| 5,092,839 A | 3/1992 | Kipperman | |
| 5,158,545 A | 10/1992 | Trudell et al. | |
| 5,176,659 A | 1/1993 | Mancini | |
| 5,183,464 A | 2/1993 | Dubrul et al. | |
| 5,201,756 A | 4/1993 | Horzewski et al. | |
| 5,217,474 A | 6/1993 | Zacca et al. | |
| 5,318,532 A | 6/1994 | Frassica | |
| 5,318,588 A | 6/1994 | Horzewski et al. | |
| 5,336,205 A | 8/1994 | Zenzen et al. | |
| 5,344,402 A * | 9/1994 | Crocker | 604/103.01 |
| 5,407,430 A | 4/1995 | Peters | |
| 5,431,676 A | 7/1995 | Dubrul et al. | |
| 5,460,170 A | 10/1995 | Hammerslag | |
| 5,474,537 A | 12/1995 | Solar | |
| 5,522,800 A | 6/1996 | Crocker | |
| 5,533,968 A | 7/1996 | Muni et al. | |
| 5,542,926 A | 8/1996 | Crocker | |
| 5,554,136 A | 9/1996 | Luther | |
| 5,571,089 A | 11/1996 | Crocker | |
| 5,573,509 A * | 11/1996 | Thornton | 604/102.02 |
| 5,599,306 A | 2/1997 | Klein et al. | |
| 5,674,240 A | 10/1997 | Bonutti et al. | |
| 5,704,926 A | 1/1998 | Sutton | |
| 5,766,201 A | 6/1998 | Ravenscroft et al. | |
| 5,782,797 A | 7/1998 | Schweich, Jr. et al. | |
| 5,827,243 A | 10/1998 | Palestrant | |
| 5,843,050 A | 12/1998 | Jones et al. | |
| 5,846,251 A | 12/1998 | Hart | |
| 5,879,324 A * | 3/1999 | von Hoffmann | 604/500 |
| 5,891,114 A | 4/1999 | Chien et al. | |
| 5,895,398 A | 4/1999 | Wensel et al. | |
| 5,899,890 A | 5/1999 | Chiang et al. | |
| 5,938,645 A | 8/1999 | Gordon | |
| 5,957,900 A | 9/1999 | Ouchi | |
| 5,971,938 A | 10/1999 | Hart et al. | |
| 5,972,019 A | 10/1999 | Engelson et al. | |
| 5,997,508 A * | 12/1999 | Lunn et al. | 604/164.08 |
| 6,044,845 A | 4/2000 | Lewis | |
| 6,090,072 A | 7/2000 | Kratoska et al. | |
| 6,161,547 A | 12/2000 | Barbut | |
| 6,165,199 A | 12/2000 | Barbut | |
| 6,183,443 B1 * | 2/2001 | Kratoska et al. | 604/164.03 |
| 6,190,357 B1 | 2/2001 | Ferrari et al. | |
| 6,196,994 B1 | 3/2001 | Maahs | |
| 6,290,710 B1 | 9/2001 | Cryer et al. | |
| 6,295,990 B1 | 10/2001 | Lewis et al. | |
| 6,306,124 B1 | 10/2001 | Jones et al. | |
| 6,309,399 B1 | 10/2001 | Barbut et al. | |
| 6,312,374 B1 * | 11/2001 | von Hoffmann | 600/3 |
| 6,312,444 B1 | 11/2001 | Barbut | |
| 6,358,238 B1 * | 3/2002 | Sherry | 604/524 |
| 6,494,860 B2 | 12/2002 | Rocamora et al. | |
| 6,692,462 B2 | 2/2004 | Mackenzie et al. | |
| 6,932,830 B2 | 8/2005 | Ungs | |
| 7,309,334 B2 * | 12/2007 | von Hoffmann | 604/524 |
| 8,231,600 B2 | 7/2012 | von Hoffmann | |
| 2001/0037126 A1 | 11/2001 | Stack et al. | |
| 2002/0010476 A1 | 1/2002 | Mulholland et al. | |
| 2003/0050600 A1 | 3/2003 | Ressemann et al. | |
| 2003/0065353 A1 | 4/2003 | Horzewski et al. | |
| 2003/0212384 A1 | 11/2003 | Hayden | |
| 2004/0006344 A1 | 1/2004 | Nguyen et al. | |
| 2005/0124937 A1 | 6/2005 | Kick et al. | |

FOREIGN PATENT DOCUMENTS

| | | |
|---|---|---|
| EP | 0 385 920 | 2/1990 |
| EP | 0 206 553 | 1/1991 |
| WO | WO 92/19312 | 11/1992 |
| WO | WO 03/090834 | 11/2003 |

* cited by examiner

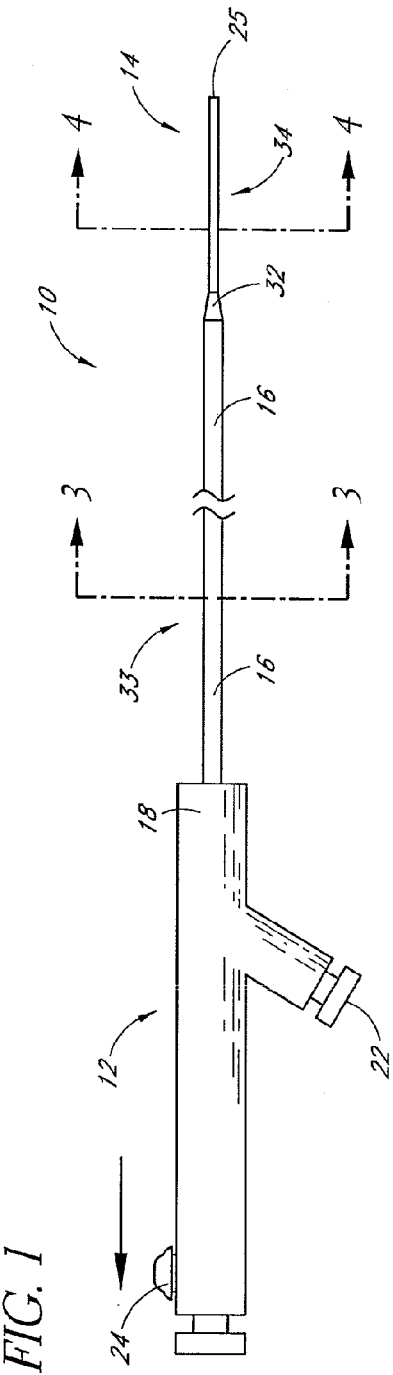
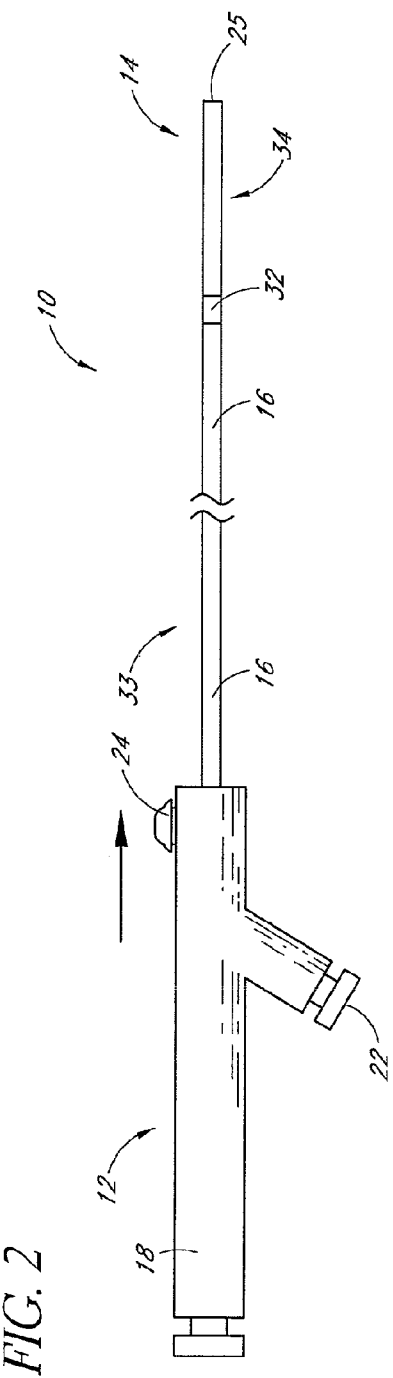
FIG. 1
FIG. 2

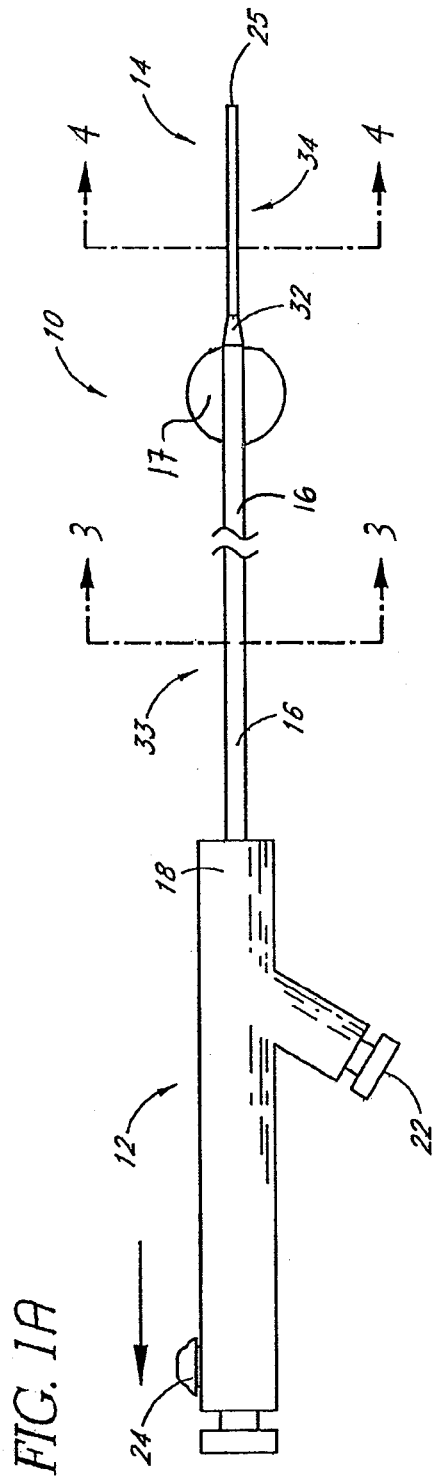

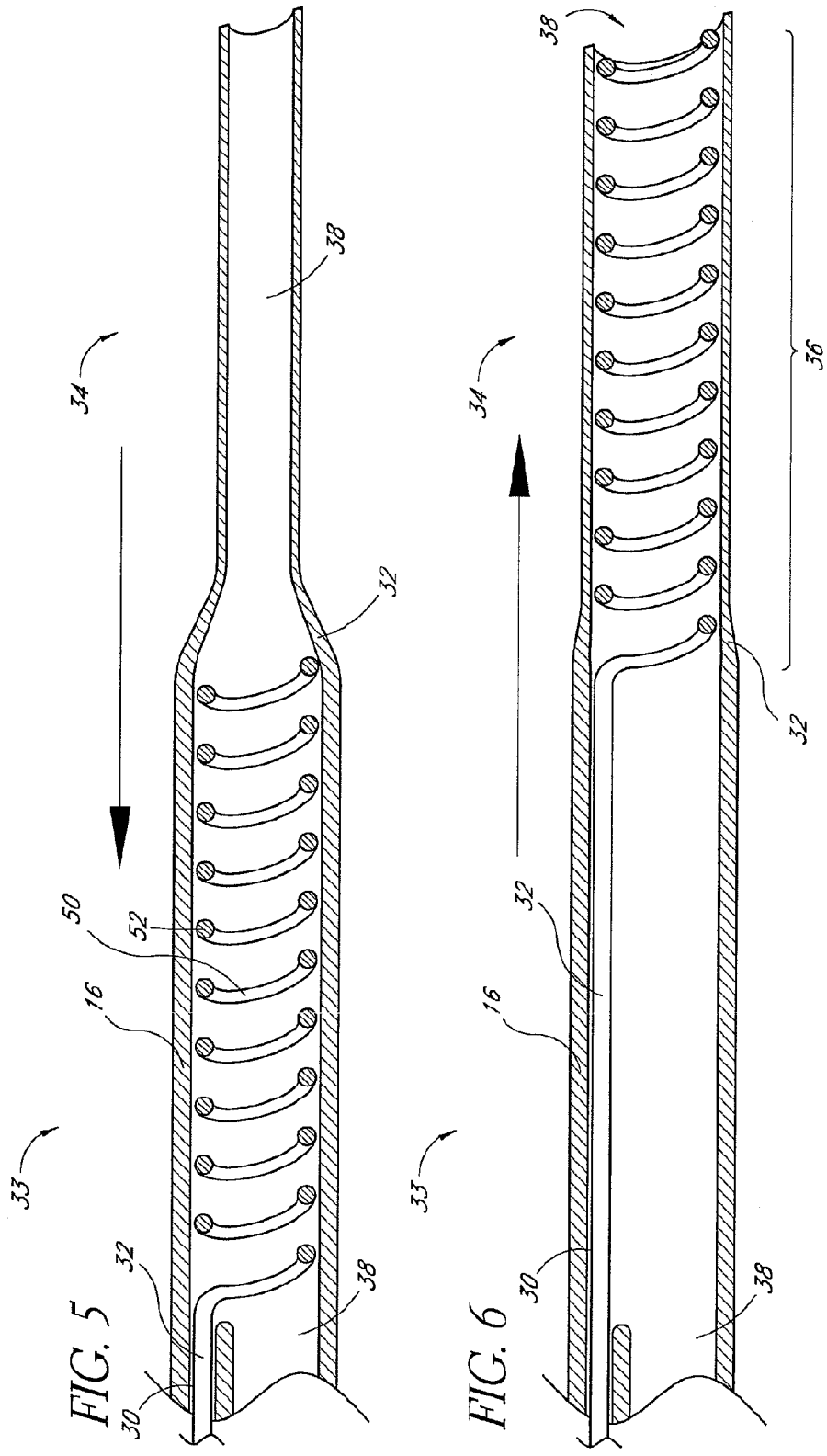

INTRAVASCULAR ACCESS CATHETER

This application is a continuation of U.S. patent Ser. No. 11/936,632 filed on Nov. 7, 2007, which is a divisional of U.S. patent application Ser. No. 10/623,875 filed Jul. 21, 2003, now U.S. Pat. No. 7,309,334 which claims priority under 35 U.S.C. §119 to U.S. Provisional Patent Application Ser. No. 60/398,071, filed Jul. 23, 2002, the disclosure of which is incorporated in its entirety herein by reference.

BACKGROUND OF THE INVENTION

Stroke is the third most common cause of death in the United States and the most disabling neurologic disorder. Approximately 700,000 patients suffer from stroke annually. Stroke is a syndrome characterized by the acute onset of a neurological deficit that persists for at least 24 hours, reflecting focal involvement of the central nervous system, and is the result of a disturbance of the cerebral circulation. Its incidence increases with age. Risk factors for stroke include systolic or diastolic hypertension, hypercholesterolemia, cigarette smoking, heavy alcohol consumption, and oral contraceptive use.

Hemorrhagic stroke accounts for 20% of the annual stroke population. Hemorrhagic stroke often occurs due to rupture of an aneurysm or arteriovenous malformation bleeding into the brain tissue, resulting in cerebral infarction. The remaining 80% of the stroke population are ischemic strokes and are caused by occluded vessels that deprive the brain of oxygen-carrying blood. Ischemic strokes are often caused by emboli or pieces of thrombotic tissue that have dislodged from other body sites or from the cerebral vessels themselves to occlude in the narrow cerebral arteries more distally. When a patient presents with neurological symptoms and signs which resolve completely within 1 hour, the term transient ischemic attack (TIA) is used. Etiologically, TIA and stroke share the same pathophysiologic mechanisms and thus represent a continuum based on persistence of symptoms and extent of ischemic insult.

Emboli occasionally form around the valves of the heart or in the left atrial appendage during periods of irregular heart rhythm and then are dislodged and follow the blood flow into the distal regions of the body. Those emboli can pass to the brain and cause an embolic stroke. As will be discussed below, many such occlusions occur in the middle cerebral artery (MCA), although such is not the only site where emboli come to rest.

When a patient presents with neurological deficit, a diagnostic hypothesis for the cause of stroke can be generated based on the patient's history, a review of stroke risk factors, and a neurologic examination. If an ischemic event is suspected, a clinician can tentatively assess whether the patient has a cardiogenic source of emboli, large artery extracranial or intracranial disease, small artery intraparenchymal disease, or a hematologic or other systemic disorder. A head CT scan is often performed to determine whether the patient has suffered an ischemic or hemorrhagic insult. Blood would be present on the CT scan in subarachnoid hemorrhage, intraparenchymal hematoma, or intraventricular hemorrhage.

Traditionally, emergent management of acute ischemic stroke consisted mainly of general supportive care, e.g. hydration, monitoring neurological status, blood pressure control, and/or anti-platelet or anti-coagulation therapy. In 1996, the Food and Drug Administration approved the use of Genentech Inc.'s thrombolytic drug, tissue plasminogen activator (t-PA) or Activase®, for treating acute stroke. A randomized, double-blind trial, the National Institute of Neurological Disorders and t-PA Stroke Study, revealed a statistically significant improvement in stoke scale scores at 24 hours in the group of patients receiving intravenous t-PA within 3 hours of the onset of an ischemic stroke. Since the approval of t-PA, an emergency room physician could, for the first time, offer a stroke patient an effective treatment besides supportive care.

However, treatment with systemic t-PA is associated with increased risk of intracerebral hemorrhage and other hemorrhagic complications. Patients treated with t-PA were more likely to sustain a symptomatic intracerebral hemorrhage during the first 36 hours of treatment. The frequency of symptomatic hemorrhage increases when t-PA is administered beyond 3 hours from the onset of a stroke. Besides the time constraint in using t-PA in acute ischemic stroke, other contraindications include the following: if the patient has had a previous stroke or serious head trauma in the preceding 3 months, if the patient has a systolic blood pressure above 185 mm Hg or diastolic blood pressure above 110 mmHg, if the patient requires aggressive treatment to reduce the blood pressure to the specified limits, if the patient is taking anticoagulants or has a propensity to hemorrhage, and/or if the patient has had a recent invasive surgical procedure. Therefore, only a small percentage of selected stroke patients are qualified to receive t-PA.

Obstructive emboli have also been mechanically removed from various sites in the vasculature for years. For example, the "Fogarty catheter" or variations thereof has been used, typically in the periphery, to remove clots from arteries found in legs and in arms. These well known devices are described, for example, in U.S. Pat. No. 3,435,826, to Fogarty and in U.S. Pat. Nos. 4,403,612 and 3,367,101. In general, these patents describe a balloon catheter in which a balloon material is longitudinally stretched when deflated.

In procedures for removing emboli using the Fogarty catheter or other similar catheters, it is typical, first, to locate the clot using fluoroscopy. The embolectomy catheter is then inserted and directed to the clot. The distal tip of the balloon catheter is then carefully moved through the center of the clot. Once the balloon has passed through the distal side of the clot, the balloon is inflated. The balloon catheter is then gradually proximally withdrawn. The balloon, in this way, acts to pull the clot proximally ahead of the balloon to a point where it can be retrieved. The majority of procedures using a Fogarty type catheter repeat these steps until the pertinent vessel is cleared of clot material.

A variety of alternative emboli retrieval catheters have also been developed, in which various wire corkscrews and baskets must be advanced distally through the embolic material in order to achieve capture and removal. However, removal of emboli using such catheters carries attendant potential problems. One such problem occurs when advancing the catheter through the clot dislodges material to a more remote site where removal may become more difficult or impossible.

New devices and methods are thus needed in treating vasculature occlusions in the body, including patients with acute ischemic stroke and occlusive cerebrovascular disease, in treating symptomatic patients with embolization or hemodynamic compromise, or in stroke prevention, e.g., patients with incidental finding of asymptomatic carotid lesion, which improve a patient's neurological function and quality of life without causing significant side effect, and can thus also be used in patients with contraindication to the use of t-PA.

SUMMARY OF THE INVENTION

There is provided in accordance with one aspect of the present invention, a method for removing thromboembolic material from a carotid or cerebral artery. The method comprises the steps of providing a catheter having a proximal end, a distal end, an expandable distal section having a distal port, an aspiration lumen communicating with the port, and an axially moveable support. The distal end of the catheter is inserted into the artery, and the support is distally advanced to expand the distal section. Negative pressure is applied to the aspiration port, to draw the thromboembolic material into the distal section.

The carotid artery may be the common carotid artery, the internal carotid artery or the carotid siphon. Alternatively, the artery may be the middle cerebral artery or the anterior cerebral artery, or elsewhere in the brain.

The method may additionally comprise the steps of introducing oxygenated medium into the artery through the aspiration lumen, or infusing pharmaceutical agent into the artery through the aspiration lumen. The pharmaceutical agent may be a vasodilator such as nifedipine or nitroprusside. The pharmaceutical agent may alternatively comprise t-PA. The thromboembolic material may be located using intravascular ultrasound, or carotid doppler.

In accordance with another aspect of the present invention, there is provided an intracranial aspiration catheter. The catheter comprises an elongate flexible tubular body, having a proximal end, a distal end, and an aspiration lumen extending therethrough. The aspiration lumen in a distal section of the body is moveable between a first, reduced inside diameter for transluminal navigation and a second, enlarged inside diameter for aspirating material. A support is provided, for controllably supporting the aspiration lumen against collapse when in the second diameter. A control is provided on the proximal end of the catheter for controlling the support. In one implementation, the support comprises a spiral element such as a spring coil. The support may be axially moveable, such as between a proximal position when the distal section is in the low cross sectional configuration, and a distal position in which the distal section is enlarged, and supported against collapse under aspiration. Alternatively, the support is activated by rotating a first end of the support relative to a second end of the support.

The aspiration lumen may be defined within a tubular wall having a plurality of folds therein, when the aspiration lumen is in the first inside diameter configuration. Alternatively, the aspiration lumen may be defined within a wall made from a stretchable material.

In accordance with another aspect of the present invention, there is provided a method of establishing a flow path through a catheter, positioned across a non-linear segment of vasculature. The method comprises the steps of transluminally navigating an enlargeable tubular wall through a non-linear segment of vasculature, and manipulating a support within a tubular wall to enlarge the inside diameter of the tubular wall to create a flow path across the non-linear segment. The manipulating step may comprise distally advancing a tubular support structure within the tubular wall. In one implementation, the method comprises distally advancing a coil within the tubular wall.

In accordance with a further aspect of the present invention, there is provided a method of aspirating material. The method comprises the steps of transluminally advancing a catheter to the site of an obstruction, the catheter having an aspiration lumen therein. A support is moved within the aspiration lumen, and, thereafter, material is aspirated from the obstruction through the aspiration lumen.

In accordance with another aspect of the present invention, there is provided an intracranial aspiration catheter. The catheter comprises an elongate flexible tubular body, having a proximal end, a distal end, and an aspiration lumen extending therethrough. The distal section on the body is moveable between a first, reduced inside diameter for transluminal navigation, and a second, enlarged inside diameter for aspirating material. A support is axially moveable between a proximal position when the aspiration lumen is in the first diameter, and a distal position for supporting the aspiration lumen against collapse when in the second diameter.

In one implementation, the support comprises a coil. The distal section may have a length of no greater than about 20 cm, in certain embodiments a length of no greater than about 10 cm, and often within the range of from about 5 cm to about 15 cm.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 1 is a side elevational schematic view of an intracranial aspiration catheter in accordance with the present invention, with a distal segment in a reduced crossing profile configuration.

FIG. 1A is a side elevational view as in FIG. 1, including an inflatable balloon.

FIG. 2 is a side elevational view as in FIG. 1, with the distal segment in an enlarged cross-sectional configuration.

FIG. 5 is a side elevational cross-sectional view through a distal portion of the catheter of FIG. 1, illustrating an axially moveable support coil in a proximal position.

FIG. 6 is a cross-sectional view as in FIG. 5, with the axially moveable support coil in a distal position.

DETAILED DESCRIPTION OF THE PREFERRED EMBODIMENT

Figure 3A:
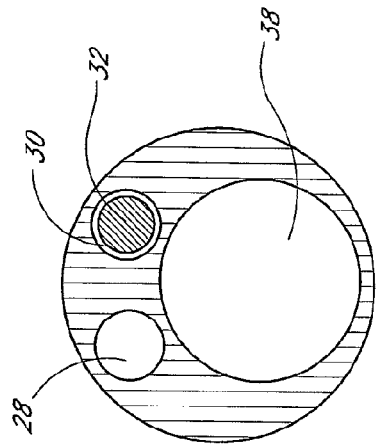
FIG. 3A is a cross-sectional view taken along the line 3-3 in FIG. 1.

Referring to FIG. 1, there is disclosed a catheter 10 in accordance with one aspect of the present invention. Although primarily described in the context of a an expandable distal segment aspiration catheter with a single central lumen, catheters of the present invention can readily be modified to incorporate additional structures, such as permanent or removable column strength enhancing mandrels, two or more lumen such as to permit drug or irrigant infusion or radiation delivery or to supply inflation media to an inflatable balloon, (See, e.g., inflatable balloon 17 in FIG. 1A) or combinations of these features, as will be readily apparent to one of skill in the art in view of the disclosure herein. In addition, the present invention will be described primarily in the context of removing obstructive material from remote vasculature in the brain.

The catheters disclosed herein may readily be adapted for use throughout the body wherever it may be desirable to introduce a low profile catheter and then provided a relatively large diameter aspiration or supported working channel. For example, low diameter catheter shafts in accordance with the present invention may be dimensioned for use throughout the coronary and peripheral vasculature, the gastrointestinal tract, the urethra, ureters, Fallopian tubes and other lumens and potential lumens, as well. The expandable lumen structure of the present invention may also be used as a minimally invasive percutaneous tissue tract expander, such as for diagnostic or therapeutic access to a solid tissue target (e.g., breast biopsy or tissue excision).

The catheter 10 generally comprises an elongate tubular body 16 extending between a proximal end 12 and a distal functional end 14. The length of the tubular body 16 depends upon the desired application. For example, lengths in the area of from about 120 cm to about 140 cm or more are typical for use in femoral access percutaneous transluminal coronary applications. Intracranial or other applications may call for a different catheter shaft length depending upon the vascular access site, as will be understood in the art.

In the illustrated embodiment, the tubular body 16 is divided into at least a fixed diameter proximal section 33 and an adjustable diameter distal section 34 separated by a transition 32, discussed infra. Alternatively, the adjustable diameter feature of distal section 34 can extend the entire length of the catheter from the manifold 18 or other proximal connector to distal tip 25, as will become apparent from the disclosure herein.

The proximal end 12 of catheter 10 is additionally provided with a manifold 18 having one or more access ports as is known in the art. Generally, manifold 18 is provided with a guidewire port 20 in an over-the-wire construction, and an aspiration port 22. Alternatively, the aspiration port 22 may be omitted if the procedure involves removal of the guidewire proximally from the guidewire port 20 following placement of the aspiration catheter, and aspiration through the guidewire port. Additional access ports may be provided as needed, depending upon the functional capabilities of the catheter. Manifold 18 may be injection molded from any of a variety of medical grade plastics, or formed in accordance with other techniques known in the art.

Manifold 18 is additionally provided with a control 24, for controlling the radial expansion of the distal segment 34 of the catheter. Control 24 may take any of a variety of forms depending upon the mechanical structure of the support. In the illustrated embodiment, control 24 comprises a slider switch which is mechanically axially moveably linked to the distal support (discussed below) such that proximal retraction of the slider switch 24 produces a proximal movement of the support. This allows the unsupported distal section 34 to assume its low profile configuration as illustrated in FIG. 1. Distal axial advancement of the slider switch 24 produces a distal axial advance of the support, as illustrated in FIG. 2. In the distal position, the support advances the distal segment 34 from the reduced diameter as illustrated in FIG. 1, to the enlarged diameter as illustrated in FIG. 2. In the enlarged configuration, the support maintains patency of a central lumen extending through the distal segment 34 to accommodate aspiration as will be discussed below.

Any of a variety of controls may be utilized, including switches, levers, rotatable knobs, pull/push wires, and others which will be apparent to those of skill in the art in view of the disclosure herein.

Referring to FIG. 3A, there is illustrated a cross-sectional view through the proximal section 33 of the catheter shaft 16 of the embodiment of FIG. 1. In the illustrated embodiment, the proximal section 33 comprises a two lumen extrusion, having a control wire lumen 30 with an axially moveable control wire 32 therein, and an aspiration lumen 38. Aspiration lumen 38 also can serve as the guidewire lumen. Alternatively, the proximal section 33 can be formed having a concentric configuration if desired.

Figure 3B:
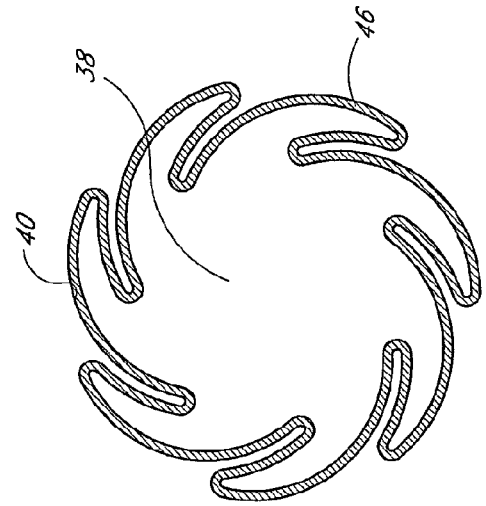
FIG. 3B is an alternate cross-section through an intracranial aspiration catheter having an over-the-wire configuration.

In an alternate configuration, as illustrated in FIG. 3B, a three lumen extrusion is utilized in the proximal section 33. A separate guidewire lumen 28 is provided, for allowing an over-the-wire configuration in which the guidewire does not need to be removed in order to accomplish aspiration. The guidewire lumen 28 therefore extends between a proximal access port 20 on the manifold 18, and a distal internal access port (not illustrated) at which point the guidewire lumen 28 opens distally into the aspiration lumen 38. Generally, the distal access port will be spaced substantially distally from the manifold along the length of the catheter. The distal access port may be positioned anywhere within the range of from about 10 cm to about 60 cm from the distal end of the catheter. This enables a partial proximal withdrawal of the guidewire following placement of the catheter, to allow use of the aspiration lumen 38 as will be apparent to those of skill in the art. However, the guidewire may remain within the guidewire lumen 28, such that it can be readily distally advanced into the distal vasculature, such as for repositioning or replacement of the catheter 10.

The distal section 34 comprises a thin flexible wall defining a central lumen 38 extending axially therethrough. The flexible wall is capable of moving between a reduced crossing profile configuration, such as that illustrated in FIG. 1, and an enlarged crossing profile configuration such as that illustrated in FIG. 2. The reduced crossing profile configuration of FIG. 1 is provided for transluminal navigation of distal torturous vasculature to reach a target site. Once the target site has been reached, the distal segment 34 is radially enlarged and supported to provide an enlarged working channel such as an aspiration lumen as will be discussed below.

Figure 4A:
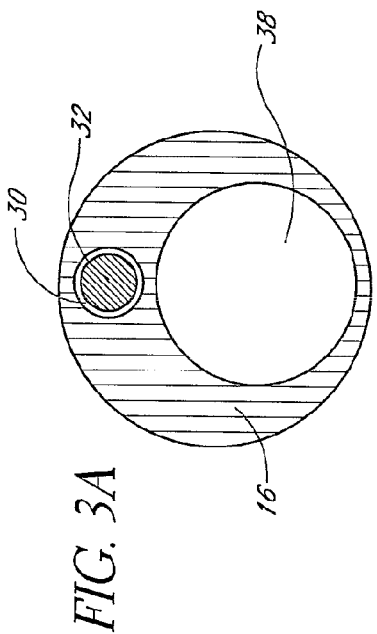
FIG. 4A is a cross-sectional view taken along the line 4-4, schematically showing a folding pattern for the distal section.

Movement of the distal section 34 from the reduced diameter to the enlarged diameter may be accomplished in a variety of ways, depending upon the desired construction. Referring to FIG. 4A, for example, a thin walled tubular segment is provided having an enlarged diameter, such as equivalent to the enlarged diameter of FIG. 2. The tubular segment is folded such as by partially collapsing a first wing 42 and a second wing 44, leaving a reduced diameter central lumen 38 having a sufficient inside diameter to axially advance over a guidewire. The first and second wings 42 and 44 are thereafter wrapped around a central portion 46 of the distal section 34 as illustrated in FIG. 4A. The resulting folded configuration may be retained by applying a heat set as is known in the balloon angioplasty arts. The distal section 34 may be attached in the vicinity of transition 32 using well known catheter fabrication techniques.

In general, the collapsed diameter of lumen 38 will be approximately 0.003 inches or greater larger than the outside diameter of the intended guidewire. Guidewires having diameters in the range of from about 0.009 inches to about 0.016 inches are presently contemplated.

Avoiding a tight fit between the guidewire 40 and inside diameter of guidewire lumen 28 enhances the slideability of the catheter over the guidewire. In ultra small diameter catheter designs, it may be desirable to coat the outside surface of the guidewire 40 and/or the inside surface of the wall defining lumen 38 with a lubricous coating to minimize friction as the catheter 10 is axially moved with respect to the guidewire 40. A variety of coatings may be utilized, such as Paralene, Teflon, silicone rubber, polyimide-polytetrafluoroethylene composite materials or others known in the art and suitable depending upon the material of the guidewire or inner tubular wall 38.

Figure 4B:
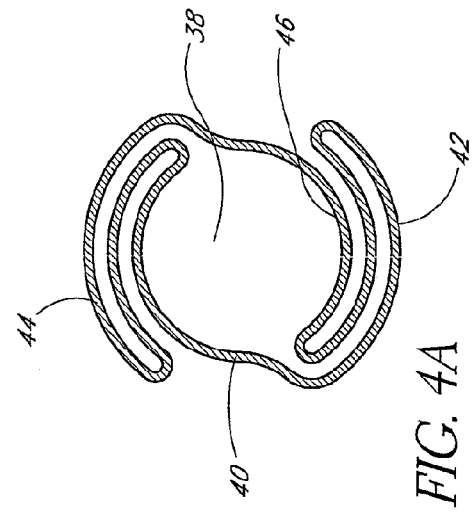
FIG. 4B is a cross-sectional view as in FIG. 4A, showing an alternate folding pattern.

In an alternate configuration, as illustrated in FIG. 4B, the tubular wall 40 is provided with a plurality of wings 46. Each of these may be folded and provided with a heat set to produce a reduced diameter configuration. Alternatively, the tubular wall 40 may be extruded in the winged configuration, depending upon the desired manufacturing technique.

Referring to FIGS. 5 and 6, a moveable support 50 is provided for enlarging the distal section 34 from the reduced diameter to the enlarged diameter configuration. In the illustrated embodiment, the moveable support 50 is in the form of an axially moveable coil 52. Coil 52 is mechanically linked to the control 24 by an axially moveable control wire 32. Distal advance of the control 24 causes the control wire 32 to advance distally through the control wire lumen 30, thereby advancing the moveable coil 52 from a position within the proximal section 33, across the transition 32 and into the distal section 38. This causes the distal section 38 to move from the reduced diameter to the enlarged diameter configuration.

The coil 52 resists collapse of the tubular wall 40 when vacuum is applied to the central lumen 38. Due to the radial support characteristics of the moveable coil 52, the wall thickness of the tubular wall 40 may be minimized to a limit which is determined by physical characteristics of the polymer, together with the spacing between adjacent filars of the moveable coil 52. Optimal relationships between these variables can be determined through routine experimentation by those of ordinary skill in the art, in view of the disclosure herein.

The use of an axially moveable coil 52 is believed to enable both radial enlargement of the distal aspiration lumen 38, as well as placement of a large ID aspiration lumen in small vessels, even around corners in the vasculature. The catheter can be placed within torturous vasculature while in the low profile configuration, to reach a remote site. Distal advance of the support coil within the catheter can then track through the tortuous vasculature while radially enlarging the aspiration lumen. This is enabled through the use of a laterally flexible tubular support, such as a helix, spring, micro slotted tube or other tubular support with lateral flexibility. In this manner, the distal section 34 may be positioned within portions of the anatomy and then enlarged to a diameter which would not have been able to axially traverse the vasculature without unacceptable levels of vascular trauma, using conventional catheter constructions.

The exact configuration of the moveable support 50 may be varied considerably, and still accomplish the objectives of the present invention. For example, referring to FIGS. 7 and 8, the moveable support 50 is in the form of a helical ribbon 54. The helical ribbon 54 may be provided by helically cutting through the wall of a segment of the distal end of a tube 56 using techniques which are disclosed elsewhere herein. Thus, as illustrated in FIG. 8, a support zone 58 is provided on the distal end of a tube 56. Tube 56 may extend concentrically within the central lumen 38 proximally to the manifold 18, or to a control on the proximal catheter shaft. Alternatively, 256 may be in mechanical communication with the control 24 by way of an axially moveable control wire 32 as has been discussed. Ribbon 54 may alternatively be formed by wrapping around a mandrel, or other techniques which will be known to those of skill in the art.

Aspiration catheters of the present invention which are adapted for intracranial applications generally have a total length in the range of from 60 cm to 250 cm, usually from about 135 cm to about 175 cm. The length of the proximal segment 33 will typically be from 20 cm to 220 cm, more typically from 100 cm to about 120 cm. The length of the distal segment 34 will typically be in the range from 2 cm to about 50 cm, usually from about 5 cm to about 20 cm. The proximal and distal body segments 33, 34 may be joined to each other, i.e. at a transition 32. The body segments may be joined in any of a variety of conventional manners, such as heat fusion, adhesive bonding, coextrusion, or the like. In the exemplary embodiment, the two body segments 33, 34 will be formed separately and thereafter fused together by the application of heat with a removable mandrel extending through each lumen which crosses the transition 32 to maintain patency. An outer shrink wrap tubing may be used to add structural integrity by spanning the transition 32.

The catheters of the present invention may be composed of any of a variety of biologically compatible polymeric resins having suitable characteristics when formed into the tubular catheter body segments. Exemplary materials include polyvinyl chloride, polyethers, polyamides, polyethylenes, polyurethanes, copolymers thereof, and the like. In certain embodiments, in which the distal segment 34 dilates (stretches) radially rather than unfolds, the distal segment 34 may be formed from more elastic materials, such as latex rubber, silicone rubber, and blends thereof. In one embodiment, both the proximal body segment 33 and distal body segment 34 will comprise a polyvinyl chloride (PVC), with the proximal body segment being formed from a relatively rigid PVC and the distal body segment being formed from a relatively flexible, supple PVC. Optionally, the proximal body segment may be reinforced with a metal or polymeric braid or other conventional reinforcing layer.

The proximal body segment will exhibit sufficient column strength to permit axial positioning of the catheter through a guide catheter at least a portion of with the distal body segment 34 extending into the patient's vasculature. The proximal body segment may have a shore hardness in the range from 50 D to 100 D, often being about 70 D to 80 D. Usually, the proximal shaft will have a flexural modulus from 20,000 psi to 1,000,000 psi, preferably from 100,000 psi to 600,000 psi. The distal body segment will be sufficiently flexible and supple so that it may navigate the patient's distal vasculature. In highly flexible embodiments, the shore hardness of the distal body segment 34 may be in the range of from about 20 A to about 100 A, and the flexural modulus for the distal segment 34 may be from about 50 psi to about 15,000 psi.

The catheter body may further comprise other components, such as radiopaque fillers; colorants; reinforcing materials; reinforcement layers, such as braids and helical reinforcement elements; or the like. In particular, the proximal body segment may be reinforced in order to enhance its column strength and torqueability while preferably limiting its wall thickness and outside diameter.

The pleated or otherwise reduced diameter of the distal body segment 34 will usually be smaller than that of the proximal body segment. In some intracranial applications, the proximal body segment will have a constant diameter, with an outer diameter in the range from 0.33 mm to 2 mm, usually from 0.67 mm to 1.67 mm, and an inner diameter in the range from 0.1 mm to 1.75 mm, usually from 0.2 mm to 1 mm. The distal body segment can be tapered, where its proximal end has a diameter which generally is the same as that of the distal end of the proximal body segment and its distal end has a diameter no greater than the range set forth above.

Usually, radiopaque markers will be provided at least at the distal end 25 and the transition region 32 between the proximal and distal body segments 33, 34. Other radiopaque markers may be provided elsewhere, such as on the support coil, if it is not already radiopaque. One radiopaque marker comprises a metal band which is fully recessed within the distal end of the proximal body segment 33. Suitable marker bands can be produced from a variety of materials, including platinum, gold, and tungsten/rhenium alloy. Preferably, the radiopaque metal band will be recessed in an annular channel formed at the distal end of the proximal body segment.

The proximal section 33 of tubular body 16 may be produced in accordance with any of a variety of known techniques for manufacturing interventional catheter bodies, such as by extrusion of appropriate biocompatible polymeric materials. Alternatively, at least a proximal portion or all of the length of tubular body 16 may comprise a polymeric or metal spring coil, solid walled hypodermic needle tubing, or braided reinforced wall, as is known in the microcatheter arts.

In many applications, the proximal section 33 of tubular body 16 is provided with an approximately circular cross-sectional configuration having an external diameter within the range of from about 0.025 inches to about 0.065 inches. In accordance with one embodiment of the invention, the proximal section 33 of tubular body 16 has an external diameter of about 0.042 inches (3.2 f) throughout most of its length. Alternatively, a generally oval or triangular cross-sectional configuration can also be used, as well as other noncircular configurations, depending upon the method of manufacture, number and arrangement of internal lumens and the intended use.

In a catheter intended for peripheral vascular applications, the proximal section 33 of body 16 will typically have an outside diameter within the range of from about 0.039 inches to about 0.065 inches. In coronary vascular applications, the proximal section 33 of body 16 will typically have an outside diameter within the range of from about 0.025 inches to about 0.045 inches. The illustrated construction of distal section 34 permits lower external cross-sections in the collapsed configuration, as low as 0.028 inches or 0.025 inches or 0.022 inches or lower as may be desired for remote coronary or intracranial applications.

Diameters outside of the preferred ranges may also be used, provided that the functional consequences of the diameter are acceptable for the intended purpose of the catheter. For example, the lower limit of the diameter for any portion of tubular body 16 in a given application will be a function of the number of fluid or other functional lumen contained in the catheter, together with the acceptable minimum aspiration flow rate and collapse resistance.

Tubular body 16 must have sufficient structural integrity (e.g., column strength or "pushability") to permit the catheter to be advanced to distal locations without buckling or undesirable bending of the tubular body. The ability of the body 16 to transmit torque may also be desirable, such as to avoid kinking upon rotation, to assist in steering. The tubular body 16, and particularly the distal section 34, may be provided with any of a variety of torque and/or column strength enhancing structures. For example, axially extending stiffening wires, spiral wrapped support layers, braided or woven reinforcement filaments may be built into or layered on the tubular body 16. See, for example, U.S. Pat. No. 5,891,114 to Chien, et al., the disclosure of which is incorporated in its entirety herein by reference.

In many applications, the proximal section 33 will not be required to traverse particularly low profile or tortuous arteries. For coronary vascular applications, for example, the proximal section 33 will be mostly or entirely within the relatively large diameter guide catheter. The transition 32 can be located on the catheter shaft 16 to correspond approximately with the distal end of the guide catheter when the balloon 24 and/or distal end 14 is at the treatment site. Viewed the other way, the length of the distal section 34 is preferably at least as long as the distance from the ostium of the relevant coronary artery to the treatment site. In most applications, the transition 32 will be at least about 3 cm, preferably at least about 5 cm and alternatively as much as about 10 cm but often not more than about 20 cm from the distal end of the catheter. Distances as much as 30 cm to 50 cm or greater between the transition 32 and distal end of the catheter may also be desirable in some applications.

For certain other applications, such as intracranial catheterizations, the distal section 34 is preferably at least about 5 cm long and small enough in diameter to pass through vessels as low as 3 mm or 2 mm or lower. Catheters for this application may have a proximal section length of between about 60 cm to about 150 cm and a distal section length of between about 5 cm to about 15 cm, and the distal section is able to track a tortuous path of at least about 5 cm through vessels of less than about 3 mm lumen ID. further structure, dimensional and method disclosure can be found in U.S. Pat. No. 4,739,768 to Engelson, the disclosure of which is incorporated in its entirety herein by reference.

The distal section 34, may be manufactured as an extrusion. In one method of manufacture, the extrusion is formed from a medium to high melt index polyethylene or other polymer having an outside diameter of greater than the diameter of the desired finished product. The raw extrusion can thereafter be drawn down to the desired diameter, in accordance with known processing techniques. The draw down pull speed can be varied such as along a proximal portion of the extrusion to produce a taper to a larger proximal diameter. This permits a smooth transition 32 from the relatively smaller outside diameter distal section 34 to the typically larger outside diameter of proximal section 33. High melt index materials allow the production of a greater number of different diameter draw downs by adjusting pull speed and other process parameters, for a given set of tooling as will be appreciated by those of skill in the art. The distal end 14 can be further reduced in diameter by an additional draw down step if desired.

Figure 7:
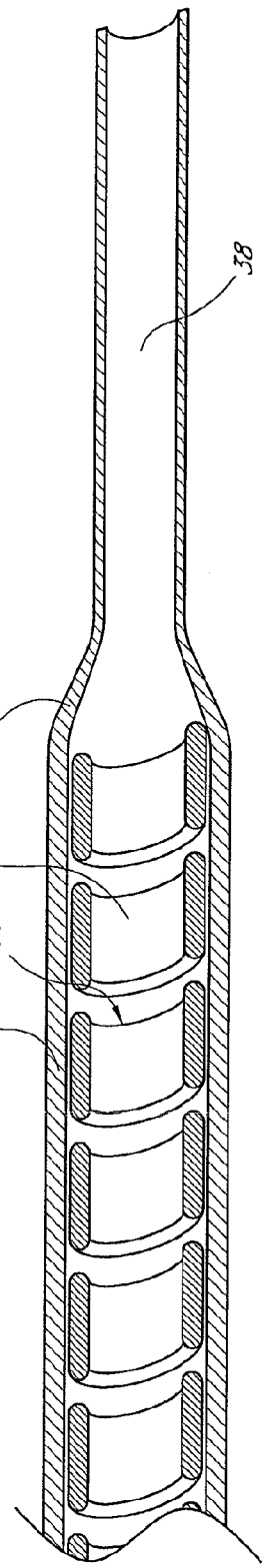
FIG. 7 is a cross-sectional view as in FIG. 5, showing an alternate support coil in a proximal position.
Figure 8:
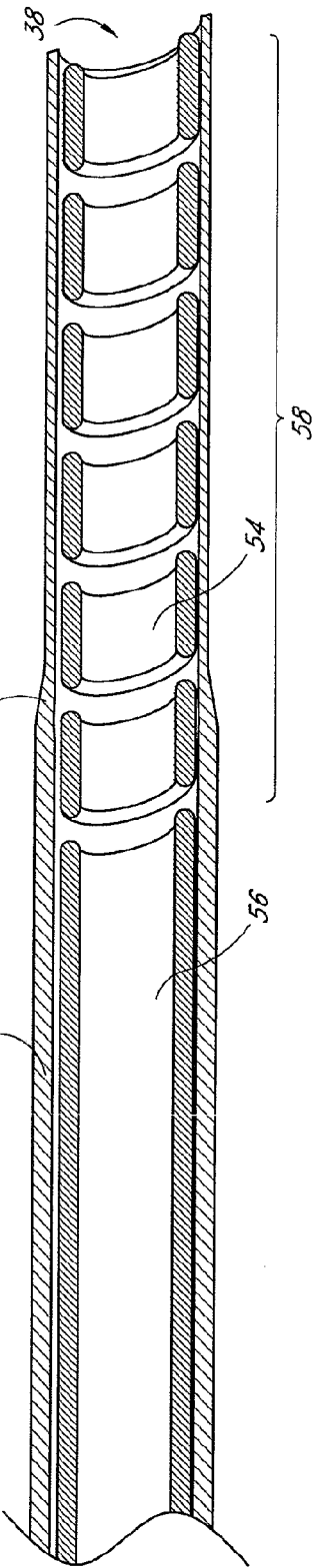
FIG. 8 is a cross-sectional view as in FIG. 7, with the alternate support coil in a distal position.

Referring to FIGS. 7 and 8, the axially moveable support may be provided in the form of an elongate flexible tube 56. A distal section 58 of tubular element 56 is provided with a spiral cut, to retain radial strength but provide lateral flexibility. The spiral cut section 58 generally has a length within the range of from about 1 centimeter to 15 centimeters, preferably within a range of about 5 centimeters to about 12 centimeters, and, in a particular embodiment, extends for approximately 10 centimeters in length. The spiral cut generally has a pitch within the range of from about 0.01 inches to about 0.125 inches, and in one embodiment, has a 0.06 pitch. In another embodiment, the distal section 32 comprises a first spiral cut section having a length of about 5 cm and a pitch of about 0.06, and a second, distal section having a length of about 5 cm and a pitch of about 0.030.

Preferably, the spiral cut extends completely through the wall of the tubular element 56 to produce a helical or coiled configuration. The precise pitch of the spiral cut and axial spacing of adjacent windings can be varied widely while still accomplishing the purposes of the present invention, and can be optimized for any particular application in view of the disclosure herein.

For example, polytetrafluoroethylene tubing, such as that suitable for tubular element 30, can be commercially obtained from Zeus, in Orangeburg, S.C. The distal section 32 can be provided with a spiral cut, such as by any of a variety of techniques that can be devised by those of skill in the art. In accordance with one technique, the PTFE or other tubing is placed onto a mandrel. The mandrel is attached to a machine with a predetermined screw thread. A cutting element such as a razor blade or other sharp instrument is placed across the tubing and the machine is activated to rotate the mandrel. As rotation of the machine (screw thread) occurs, the mandrel moves axially and rotationally causing the tubing to be cut in a spiral manner by the cutting implement. The machine can be set up to cut either a right or left hand spiral. The machine can also be set to cut continuous or variable pitch spirals, or multizone spiral sections in which each zone has a unique pitch. A metal spring coil 34 can be wrapped about a suitably sized rotating mandrel as is known in the art, with the distal open wound section 36 formed by stretching.

The tubular support 58 may alternatively be in the form of a wire spring, extending throughout the length of the distal segment or entire catheter. See Generally FIGS. 5 and 6. A distal section 36 of the coil spring 52 is stretched axially to produce an open wound configuration, such that the axial space between adjacent windings of the coil may be within the range of from about 0.05 mm to about 1 mm or greater. The proximal portion of coil spring 34 is generally bottomed out (not illustrated), such that adjacent windings of the coil are in contact with one another. This provides column strength, to allow distal advancement within the catheter, while retaining lateral flexibility. Alternatively, the coil spring can be open wound with, e.g., 0.01 mm to 1 mm spacing for the entire length.

A variety of materials can be used to construct the coil spring 52, such as stainless steel, platinum, platinum alloy, nickel, or titanium alloys. Coil spring 52 can be produced from any of a variety of stock forms, such as round cross-sectional wire, square or other rectangular wire, or polymeric materials as are known in the art. In one embodiment, coil spring 52 is wound from a flat wire made from stainless steel and having cross-sectional dimensions of about 0.002 by about 0.006 inches.

The cerebral circulation is regulated in such a way that a constant total cerebral blood flow (CBF) is generally maintained under varying conditions. For example, a reduction in flow to one part of the brain, such as in acute stroke, may be compensated by an increase in flow to another part, so that CBF to any one region of the brain remains unchanged. More importantly, when one part of the brain becomes ischemic due to a vascular occlusion, the brain compensates by increasing blood flow to the ischemic area through its collateral circulation.

Figure 9:
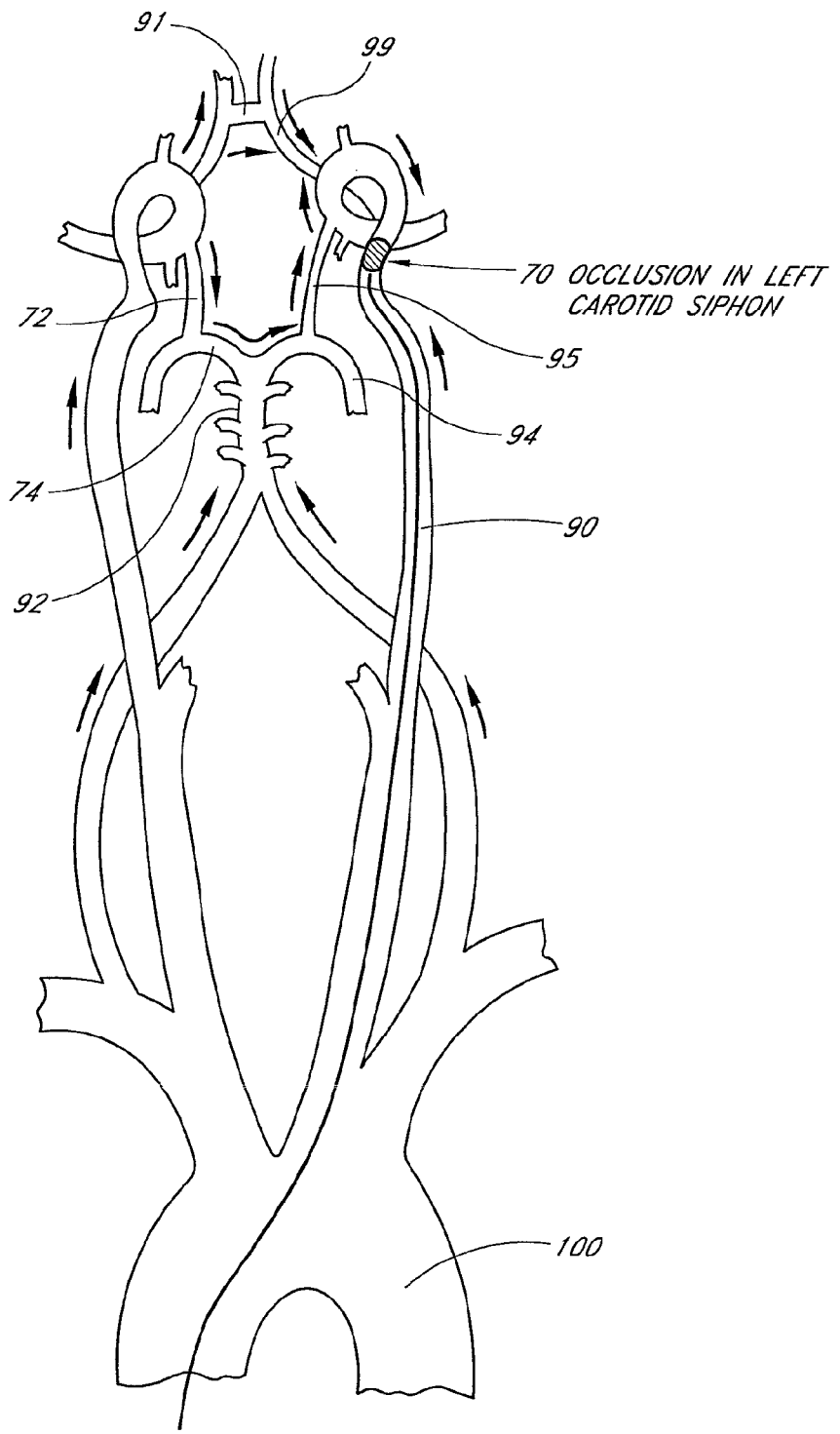
FIG. 9 is a schematic representation of the reversed circulation in the circle of Willis, to compensate for an occlusion in the left carotid siphon artery, with a guidewire extending through the left internal carotid artery to the occlusion.

FIG. 9 depicts a normal cerebral circulation and formation of Circle of Willis. Aorta 100 gives rise to right brachiocephalic trunk 82, left common carotid artery (CCA) 80, and left subclavian artery 84. The brachiocephalic artery further branches into right common carotid artery 85 and right subclavian artery 83. The left CCA gives rise to left internal carotid artery (ICA) 90 which becomes left middle cerebral artery (MCA) 97 and left anterior cerebral artery (ACA) 99. Anteriorly, the Circle of Willis is formed by the internal carotid arteries, the anterior cerebral arteries, and anterior communicating artery 91 which connects the two ACAs. The right and left ICA also send right posterior communicating artery 72 and left posterior communicating artery 95 to connect, respectively, with right posterior cerebral artery (PCA) 74 and left PCA 94. The two posterior communicating arteries and PCAs, and the origin of the posterior cerebral artery from basilar artery 92 complete the circle posteriorly.

When an occlusion occurs acutely, for example, in left carotid siphon 70, as depicted in FIG. 9, blood flow in the right cerebral arteries, left external carotid artery 78, right vertebral artery 76 and left vertebral artery 77 increases, resulting in directional change of flow through the Circle of Willis to compensate for the sudden decrease of blood flow in the left carotid siphon. Specifically, blood flow reverses in right posterior communicating artery 72, right PCA 74, left posterior communicating artery 95. Anterior communicating artery 91 opens, reversing flow in left ACA 99, and flow increases in the left external carotid artery, reversing flow along left ophthalmic artery 75, all of which contribute to flow in left ICA 90 distal the occlusion to provide perfusion to the ischemic area distal to the occlusion. A guidewire is illustrated in position proximal to the occlusion.

In use, the distal end of the aspiration catheter 10 is inserted through an incision on a peripheral artery over the guidewire into a more distal carotid or intracranial artery, such as the terminal ICA, carotid siphon, MCA, or ACA. Thromboembolic material 202 is shown occluding the lumen of a cerebral artery narrowed by atheromatous plaque 200. The occlusion site can be localized with cerebral angiogram or IVUS. In emergency situations, the catheter can be inserted directly into the symptomatic carotid artery after localization of the occlusion with the assistance of IVUS or standard carotid doppler and TCD.

Figure 10:
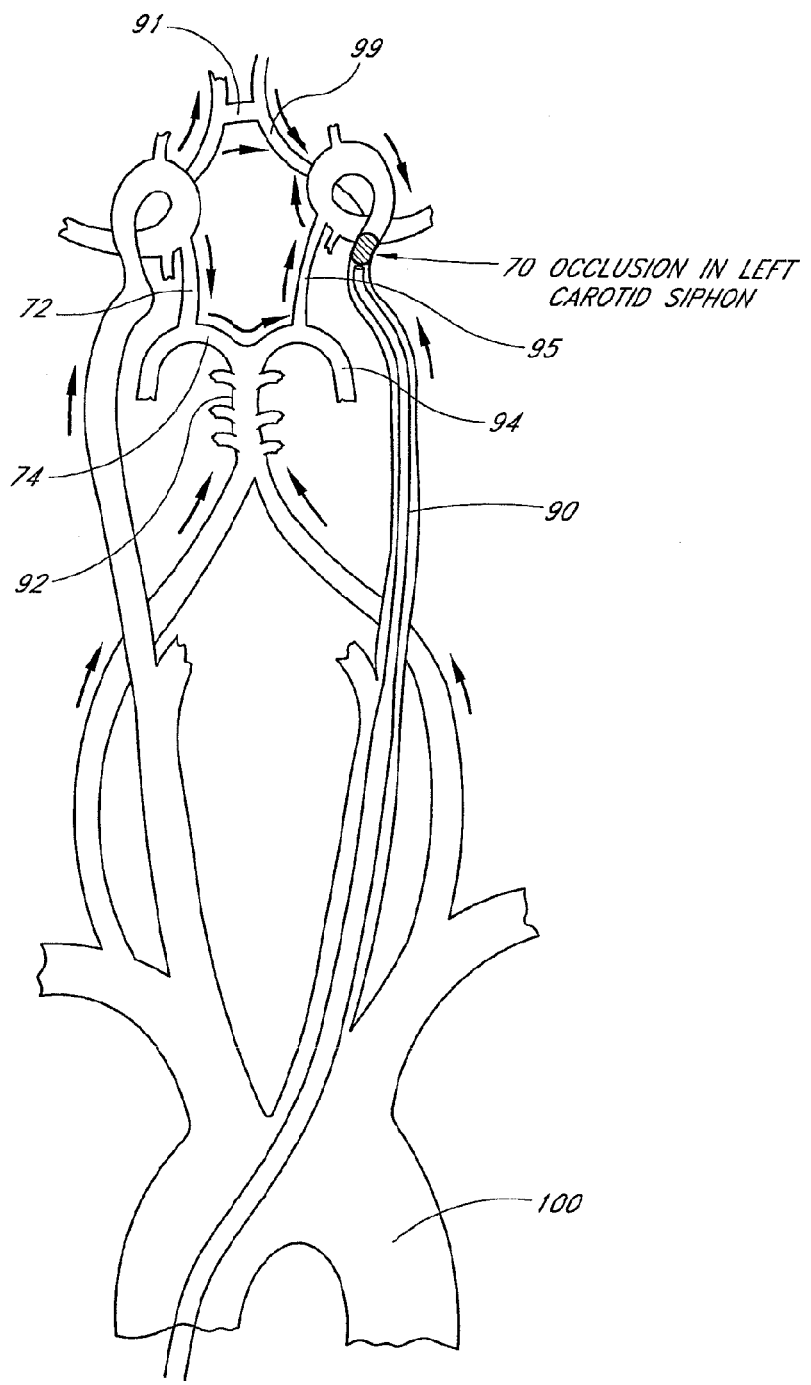
FIG. 10 is a schematic illustration as in FIG. 9, with an intracranial aspiration catheter advanced to the occlusion, in the reduced diameter configuration.

As illustrated in FIG. 10, the catheter 10 is transluminally navigated along or over the guidewire, to a position just proximal to the occlusion. Transluminal navigation is accomplished with the distal section of the catheter in the first, reduced cross sectional configuration. This enables navigation of tortuous vasculature which a larger cross section may not be able to traverse.

Figure 11:
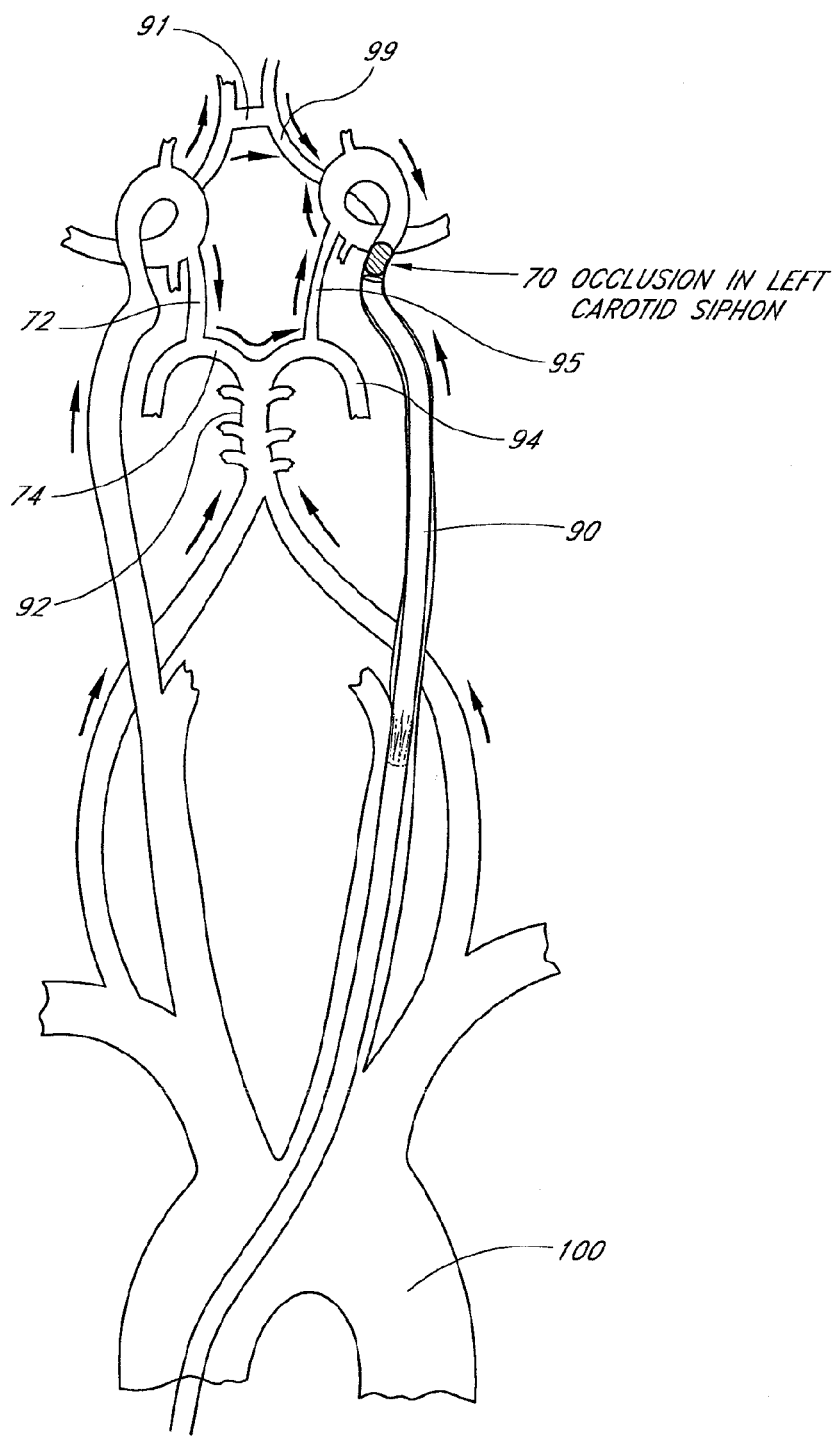
FIG. 11 is a schematic representation as in FIG. 10, with the distal section of the catheter in the enlarged diameter configuration.

Referring to FIG. 11, the cross section of the distal segment is enlarged after the catheter has been positioned, such as by distally axially advancing a tubular support as has been described previously. This allows a larger inside diameter aspiration lumen than would otherwise have been navigable to the treatment site. In addition, the use of a coil or spiral wrapping as the tubular support enables the distal segment to be expanded through curves in the vasculature, without kinking or straightening the vasculature. As will be appreciated from even the simplified schematic of the cerebral vasculature shown in FIG. 11, the length of the distal section may be varied depending upon the intended target site for the catheter. Since the inside diameter of the vasculature decreases distally, the length and collapsed crossing profile of the distal section is designed to take into account the length and inside diameter of the vessel leading up to a target occlusion.

Figure 12:
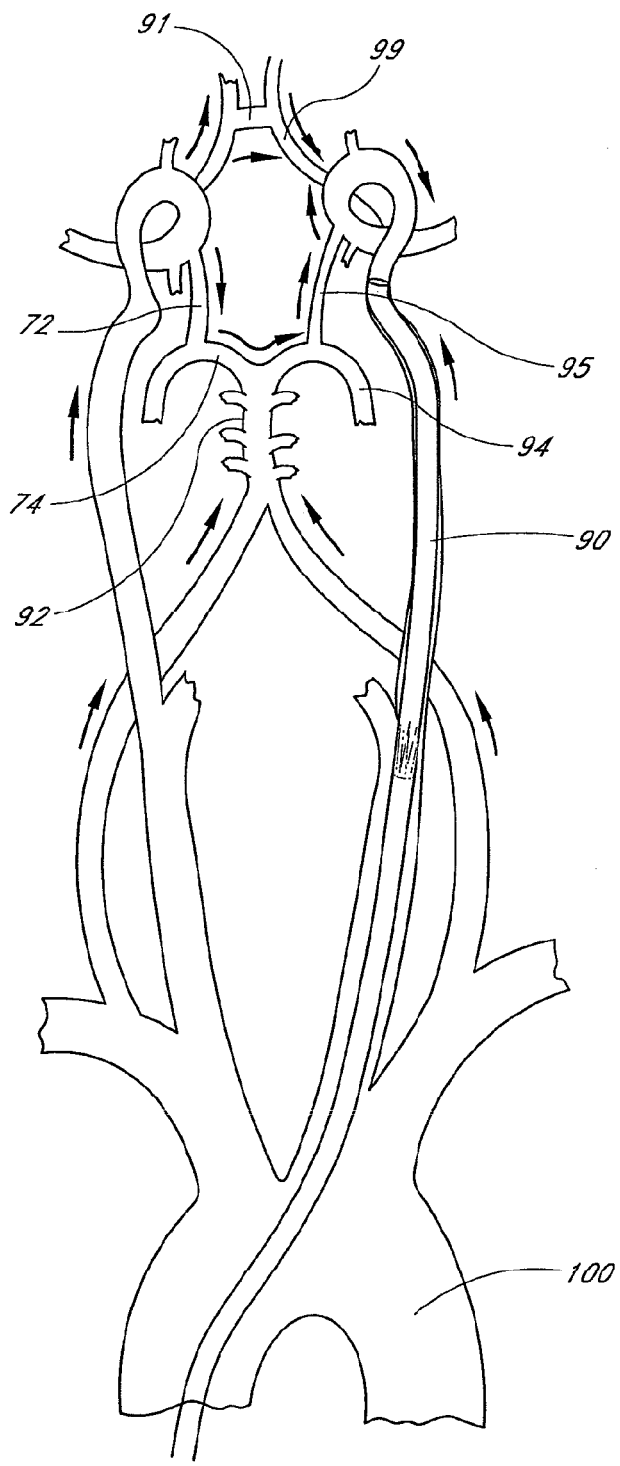
FIG. 12 is a schematic representation as in FIG. 11, following aspiration of the occlusion through the enlarged diameter of the aspiration catheter.

Aspiration is thereafter applied to the aspiration lumen, thereby drawing the occlusion into the catheter as illustrated in FIG. 12. The distal section may thereafter be reduced in cross section, and the catheter proximally retracted from the patient. A vasodilator, e.g., nifedipine or nitroprusside, may be injected through lumen 38 and port 25 to reverse vascular spasm induced as a result of instrumentation.

Pressure may be monitored by a manometer and can be altered by applying vacuum to the proximal end of the catheter. A pressure dial, which may be included in the proximal end of the catheter, allows suction within the vessel to be regulated. When continuous negative pressure is applied, occluding material 202 is dislodged into aspiration port 25 and proximally through aspiration lumen 38.

If the occlusion is not removed by the above continuous suction method, intermittent suction can be used to create an alternating negative-positive pressure gradient, which may dislodge the thromboembolic occlusion. Alternatively, a thrombolytic agent, e.g., t-PA may be infused through lumen 38 and port 25 to lyse the occlusion if soft thrombus is suspected. Standard atherectomy or angioplasty with or without stent placement can also be performed on atheromatous plaque after removal of the occlusion if perfusion through the diseased artery is still inadequate.

Focal hypothermia, which has been shown to be neuroprotective, can be administered by perfusing hypothermic oxygenated blood or fluid. Perfusion through port 25 can be achieved by withdrawing venous blood from a peripheral vein and processing through a pump oxygenator, or by withdrawing oxygenated blood from a peripheral artery, such as a femoral artery, and pumping it back into the carotid artery.

If suction fails to dislodge the occlusion, a thrombolytic agent, e.g., t-PA, can be infused through lumen 38 and port 25 to lyse any thrombotic material with greater local efficacy and fewer systemic complications. Administration of thrombolytic agent, however, may not be recommended for devices which are inserted directly into the carotid artery due to increased risk of hemorrhage. If perfusion is continued for more than a few minutes, removal of excess fluid from the circulation is required to avoid fluid overload. Fluid can be withdrawn from a jugular vein or from any other peripheral vein or artery, e.g., the femoral vein or artery, and re-introduced into the symptomatic artery. Moderate hypothermia, at approximately 32 to 34° C., can be introduced during the fluid recirculation.

In patients with vertebral artery occlusions, treatment with angioplasty often results in disastrous complications due to embolization of the occlusive lesion downstream to the basilar artery. Emboli small enough to pass through the vertebral arteries into the larger basilar artery are usually arrested at the top of the basilar artery, where it bifurcates into the posterior cerebral arteries. The resulting reduction in blood flow to the ascending reticular formation of the midbrain and thalamus produces immediate loss of consciousness. The devices described in FIG. 1 through FIG. 8 can be used to remove thromboembolic material from the vertebral artery. The occlusion site is first localized with transcranial doppler and angiogram. The catheter 10 can be inserted through an incision on a peripheral artery into the symptomatic vertebral artery or the subclavian artery. For example, the distal end of catheter 10 may be inserted proximal to thromboembolic material 202 in right vertebral artery 87 and left subclavian artery 84. When continuous or intermittent suction is applied to the distal end of the catheter, the pressure gradient across the occluding lesion increases and thromboembolic material 202 may be dislodged and captured by the aspiration port. The thromboembolic material may thereafter be removed continuous or pulsed suction, thereby reducing the risk of embolization to the basilar artery.

Access for the catheter of the present invention can be achieved using conventional techniques through an incision on a peripheral artery, such as right femoral artery, left femoral artery, right radial artery, left radial artery, right brachial artery, left brachial artery, right axillary artery, left axillary artery, right subclavian artery, or left subclavian artery. An incision can also be made on right carotid artery or left carotid artery 130 in emergency situations.

The length of the catheter for those access sites to reach the brain will generally be between 20 to 100 centimeters, preferably approximately between 30 and 60 centimeters. The inner diameter of the catheter may be between 0.2 and 0.6 centimeters, or smaller. The foregoing ranges are set forth solely for the purpose of illustrating typical device dimensions. The actual dimensions of a device constructed according to the principles of the present invention may obviously vary outside of the listed ranges without departing from those basic principles.

Although the present invention has been described in terms of certain preferred embodiments, it may be incorporated into other embodiments by persons of skill in the art in view of the disclosure herein. The scope of the invention is therefore not intended to be limited by the specific embodiments disclosed herein, but is intended to be defined by the full scope of the following claims.

What is claimed is:

1. An access catheter having an enlargeable internal working lumen, comprising:
    an elongate, flexible tubular body, having a proximal end, a distal end, and a working lumen extending therethrough;
    a proximal section on the body, having a fixed diameter;
    a distal section on the body which is movable between a first, reduced outside diameter less than the fixed diameter for transluminal navigation and a second, enlarged outside diameter to accommodate an enlarged internal working lumen;
    an axially movable tubular support for controllably supporting the working lumen against collapse when the working lumen is enlarged and the distal section is in the second diameter; and
    a control on the proximal end of the catheter for controlling the support;
    wherein the working lumen in the distal section is enlargeable from a first inside diameter to a second inside diameter in response to distal movement of the support;
    and wherein the support is movable from a first proximal limit within the catheter when the working lumen within the distal section is in the first inside diameter configuration to a second, distal position within the catheter to support the enlarged internal working lumen in the distal section.

2. An access catheter as in claim 1, wherein the support comprises a spiral element.

3. An access catheter as in claim 2, wherein the support comprises a spring coil.

4. An access catheter as in claim 2, comprising a control wire extending from the spiral element to the proximal end of the catheter.

5. An access catheter as in claim 1, wherein the working lumen in the distal section is defined within a tubular body having a plurality of folds therein when the distal section is in the first outside diameter configuration.

6. An access catheter as in claim 1, wherein the working lumen in the distal section is defined within a stretchable tubular wall.

7. An access catheter as in claim 1, wherein the elongate flexible tubular body has a length within the range of from 60 cm to 250 cm.

8. An access catheter as in claim 1, wherein the elongate flexible tubular body has a length of from about 135 cm to about 175 cm.

9. An access catheter as in claim 1, wherein the proximal section has a length within the range of 20 cm to 220 cm.

10. An access catheter as in claim 1, wherein the proximal section has a length from 100 cm to about 120 cm.

11. An access catheter as in claim 1, wherein the distal section has a length in the range of from 2 cm to about 50 cm.

12. An access catheter as in claim 1, wherein the distal section has a length in the range of from about 5 cm to about 20 cm.

13. An access catheter as in claim 1, further comprising at least a second lumen.

14. An access catheter as in claim 13, further comprising an inflatable balloon.

15. An access catheter having an enlargeable internal working lumen, comprising:
- an elongate, flexible tubular body, having a proximal end, a distal end, and a working lumen extending therethrough;
- a proximal section on the body, having a fixed diameter;
- a distal section on the body which is movable between a first, reduced outside diameter less than the fixed diameter and a second, enlarged outside diameter;
- an axially movable tubular support for controllably supporting the working lumen against collapse when the working lumen is enlarged and the distal section is in the second diameter; and
- a control on the proximal end of the catheter for controlling the support;
- wherein the working lumen in the distal section is enlargeable from a first inside diameter to a second inside diameter in response to distal movement of the support;
- and wherein the support is movable from a first proximal position within the catheter when the working lumen within the distal section is in the first inside diameter configuration to a second, distal position within the catheter to support the enlarged internal working lumen in the distal section.

16. An access catheter as in claim 15, wherein the support comprises a spiral element.

17. An access catheter as in claim 16, wherein the support comprises a spring coil.

18. An access catheter as in claim 16, comprising a control wire extending from the spiral element to the proximal end of the catheter.

19. An access catheter as in claim 15, wherein the working lumen in the distal section is defined within a tubular body having a plurality of folds therein when the distal section is in the first outside diameter configuration.

* * * * *